(12) United States Patent
Nojima et al.

(10) Patent No.: US 8,673,839 B2
(45) Date of Patent: Mar. 18, 2014

(54) LACTOFERRIN COMPLEX AND METHOD OF PRODUCING THE SAME

(75) Inventors: Yasuhiro Nojima, Higashiyamato (JP); Atsushi Sato, Fujisawa (JP)

(73) Assignee: NRL Pharma, Inc., Kanagawa (JP)

( * ) Notice: Subject to any disclaimer, the term of this patent is extended or adjusted under 35 U.S.C. 154(b) by 24 days.

(21) Appl. No.: 12/065,877

(22) PCT Filed: Aug. 22, 2006

(86) PCT No.: PCT/JP2006/316367
§ 371 (c)(1),
(2), (4) Date: Mar. 5, 2008

(87) PCT Pub. No.: WO2007/029484
PCT Pub. Date: Mar. 15, 2007

(65) Prior Publication Data
US 2009/0281029 A1    Nov. 12, 2009

(30) Foreign Application Priority Data
Sep. 6, 2005    (JP) .................................. 2005-258103

(51) Int. Cl.
*C07K 14/00*    (2006.01)

(52) U.S. Cl.
USPC ............................................. 514/1; 530/350

(58) Field of Classification Search
USPC ............................................ 530/350; 514/1
See application file for complete search history.

(56) References Cited

U.S. PATENT DOCUMENTS 7,053,150 B2 *    5/2006    Kozlowski et al. .......... 525/54.2
2004/0236015 A1    11/2004    Kozlowski et al.

FOREIGN PATENT DOCUMENTS

| JP | 10-67800 | 3/1998 |
| WO | 99/29759 | 6/1999 |
| WO | 00/24697 | 5/2000 |

OTHER PUBLICATIONS

International Search Report (Japanese only) for PCT/JP2006/316367 mailed Oct. 17, 2006 (7 pages).
Written Opinion of ISA (Japanese only) for PCT/JP2006/316367 mailed Oct. 17, 2006 (5 pages).
Patent Abstracts of Japan 10-067800 dated Mar. 10, 1998 (2 pages).
"A New Procedure for the Synthesis of Polyethylene Glycol-Protein Adducts; Effects on Function, Receptor Recognition and Clearance of Superoxide Dismutase, Lactoferrin, and a2 Macroglobulin" Dated Jul. 28, 1982 (pp. 25-33) Author(s): Charles O Beauchamp, et al. Analytical Biochemistry 131, 25-33 (1983).
"A Branched Monomethoxypoly (ethylene glycol) for Protein Modification" Dated Jul. 27, 1994 (pp. 62-69) Author(s): Christina Monfardini, et al. American Chemical Society, Bioconjugate Chem. 1995, 6, 62-69.
"Reduction of Immunoreactivity of Bovine Serum Albumin Conjugated with Comb-Shaped Polyethylene Glycol Derivatives" Dated Nov. 30, 1993 (pp. 287-291) Author(s): Hideyuki Sasaki et al. Biochemical and Biophysical Research Communications.
Notice of Reasons for Rejection (Office Action) issued Oct. 7, 2009, by the Japan Patent Office, in related Japan Patent Application No. JP-2005-258103, with English translation (8 pages).
Roberts, M.J., M.D., et al., "Chemistry for peptide and protein PEGylation"; Elsevier Science B.V., Advanced Drug Delivery Reviews 54 (2002); pp. 459-476.
Corrected Translation of a Notice of Reasons for Rejection issued Oct. 7, 2008 (previously submitted with an issue date of Oct. 7, 2009) by the Japan Patent Office in related Japan Patent Application No. JP 2005-258103 (4 pages).
Extended European Search Report and Written Opinion issued Nov. 4, 2009, by the European Patent Office in related European Patent Application No. EP-06782871.5 (6 pages).
EPO Communication (Office Action) issued by the European Patent Office mailed on Feb. 8, 2012 in related European Application No. 06782871.5 (5 pages).

* cited by examiner

*Primary Examiner* — Karen Cochrane Carlson
(74) *Attorney, Agent, or Firm* — Osha Liang LLP

(57) ABSTRACT

A biologically active complex of lactoferrin with a branched non-peptide hydrophilic polymer, one example of which is represented by the following formula [1]:

$$LF-[X-L_p-R-(Y_p-POLY)_q]_n \qquad [I]$$

Wherein LF is lactoferrin, X is a linkage generated by reaction of functional groups, L is a linker, R is an aliphatic hydrocarbon group having at least 3 carbon atoms, Y is a heteroatom linkage, POLY is a non-peptide hydrophilic polymer, p is 0 or 1, q is an integer of 2 to 10, and n is an integer of 1 to 10.

18 Claims, 12 Drawing Sheets

LACTOFERRIN COMPLEX AND METHOD OF PRODUCING THE SAME

TECHNICAL FIELD

The present invention relates to a biologically active complex of lactoferrin with a non-peptide hydrophilic polymer such as polyethylene glycol, a method of producing the same, and use thereof.

BACKGROUND ART

For a purpose such as the regulation of the properties of a biopolymer, the biopolymer has conventionally been conjugated with a non-peptide hydrophilic polymer such as polyethylene glycol (PEG) (herein after may be referred to as "conjugation", or "pegylation" when PEG or its similar compound is used). More specifically, conjugation is carried out generally by binding an active group to the terminal of a non-peptide hydrophilic polymer and then reacting the active group with a functional group present on the molecular surface of a protein or the like.

Particularly, the conjugation of a protein or a peptide is important, and the partial coverage of the molecular surface of a protein with a chain of a non-peptide hydrophilic polymer has been studied for shielding an epitope of the protein to reduce the antigenicity and immunogenicity thereof, for reducing the incorporation thereof into the reticuloendothelial system etc., or for preventing the recognition and degradation thereof by proteases. It is also known that the in vivo clearance of such complex substance is delayed to prolong its in vivo lifetime. On the other hand, it is frequently observed that an active site of such complex protein or the like is affected by the presence of the non-peptide hydrophilic polymer to result in reduced biological activity.

For example, interferon when complexed with PEG prolongs its in vivo lifetime about 70-fold but reduces its biological activity such as antiviral activity to about $\frac{1}{10}$. From a comprehensive viewpoint, however, the conjugation of interferon with PEG is known to result in significant improvement in its therapeutic effect and is useful for the treatment against hepatitis C.

In the concept of protein conjugation, there has been a long history since the successful conjugation of asparaginase with PEG for use of this enzyme as a drug for leukemia. Until now, the structures of conjugating reagents such as PEG (type of their active group, the size and distribution of their molecule, development of branched type, etc.) have been improved and the technologies are advancing.

Complexes of certain proteins with branched PEG are known to have higher protease resistance than its counterpart complexes with linear PEG, and to have increased stability against pH and heat depending on the protein (Non-patent Document 1: Monfardini et al., Bioconjug. Chem. 1995 6(1): 62-9). As to interferon, a complex thereof with branched PEG has a higher antiproliferative activity than that of its counterpart with other PEG or that of the interferon itself (Patent Document 1: Japanese Patent Application Laid-Open No. H10-67800).

However, a fluctuation in the activity of individual proteins upon conjugation will vary from protein to protein. Further, conjugation of a certain protein with PEG can bring about various influences on plural properties of the protein; for example, conjugation of interferon with PEG causes a decrease in its in vitro antiviral activity and an increase in its antiproliferative activity in human tumor cells. Accordingly, the optimum conditions and the like for obtaining a complex endowed with desired properties should be sufficiently examined for each protein.

It can be easily anticipated that depending on the structure of a chain (linear or branched chain, molecular size, distribution and so on) of a non-peptide hydrophilic polymer, the reaction sites and the number of reacting molecules, the conjugation of proteins, and so on exerts various influences on biochemical and pharmaceutical properties such as antigenicity, protease resistance, in vivo lifetime and heat stability, and on biological activities involved in drug efficacy. Accordingly, when such complexes are to be developed as pharmaceutical preparations, a non-peptide hydrophilic polymer chain should be added at a certain site or sites in order to guarantee predetermined qualities.

Lactoferrin (hereinafter abbreviated sometimes to "LF") is a glycoprotein with a molecular weight of about 80,000 occurring mainly in mammalian milk and also found in neutrophils, tears, saliva, nasal discharge, bile, semen and so on. Lactoferrin binds iron and thus belongs to the transferrin family. Known physiological activities of lactoferrin include an antibacterial action, an iron metal metabolism regulating action, a cell growth activating action, a hematopoietic action, an anti-inflammatory action, an antioxidant action, a phagocytosis promoting action, an antiviral action, a bifidobacteria growth promoting action, an anticancer action, a cancer metastasis inhibiting action and a translocation inhibiting action. Recently, lactoferrin has also been revealed to have a lipid metabolism improving action, an analgesic/antistress action and an anti-aging action. As described above, lactoferrin is a multifunctional bioactive protein showing various functions and is expected for use in pharmaceutical preparations and foods for restoration or promotion of health, and lactoferrin-containing foods have already been commercially available.

Lactoferrin, when orally ingested, undergoes hydrolysis by an acid protease, pepsin, occurring in gastric juice thereby being decomposed into peptides, and thus hardly arrives as the lactoferrin molecule at the intestinal tract. In the gastrointestinal tract, however, lactoferrin receptors are known to occur in the mucosa of small intestine, and it has recently been revealed that lactoferrin is incorporated via the intestinal tract into the body, to express its bioactivity. Therefore, for exhibiting the bioactivity of lactoferrin, it is important that lactoferrin is allowed to arrive at the intestinal tract without undergoing hydrolysis by pepsin in the gastric juice.

With respect to lactoferrin, there is also a report on its PEG complex (Non-patent Document 2: C. O. Beauchamp et al., Anal. Biochem. 131: 25-33 (1983)). However, this literature merely describes that a complex of LF with linear PEG has an in vivo lifetime prolonged 5- to 20-fold, and does not describe the bioactivity of pegylated LF or the degree and uniformity of pegylation.

Patent Document 1: Official gazette of Japanese Patent Application Laid-Open No. H10-67800

Non-patent Document 1: Monfardini et al., Bioconjug. Chem. 1995 6(1): 62-9

Non-patent Document 2: C. O. Beauchamp et al., Anal. Biochem. 131: 25-33 (1983)

DISCLOSURE OF THE INVENTION

An object of the present invention is to provide a clinically highly useful, non-peptide hydrophilic polymer/lactoferrin complex with reduced antigenicity, imparted pepsin resistance and a prolonged in vivo lifetime, as well as a method of producing the same. Another object of the present invention is to provide a lactoferrin complex with a predetermined amount of the bioactivity of natural lactoferrin, a significantly prolonged in vivo lifetime and more clinical usefulness than that of natural lactoferrin, as well as a method of producing the same.

The present inventors examined reaction conditions and the like for conjugating lactoferrin most uniformly with a non-peptide hydrophilic polymer such as polyethylene glycol (PEG) while maintaining the biological activity of lactoferrin, thereby enabling such a polymer having a specific structure to be bound to limited sites of the molecular surface of lactoferrin. The inventors obtained the results that the lactoferrin complex thus produced had resistance to proteases such as pepsin and trypsin and also had an iron-chelating ability that was the most important bioactivity, and the present invention was thereby completed.

Specifically, the present invention provides:

[1] A biologically active complex of lactoferrin with a branched non-peptide hydrophilic polymer;

[2] The complex according to [1], which is represented by the following formula [I]:

[kagaku 1]

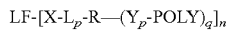

$$\text{LF-}[X\text{-}L_p\text{-}R\text{—}(Y_p\text{-POLY})_q]_n \qquad [I]$$

wherein LF is lactoferrin, X is a linkage generated by reaction of functional groups, L is a linker, R is an aliphatic hydrocarbon group having at least 3 carbon atoms, Y is a heteroatom linkage, POLY is a non-peptide hydrophilic polymer, p is 0 or 1, q is an integer of 2 to 10, and n is an integer of 1 to 10;

[3] The complex according to [1] or [2], which is represented by the following formula [II]:

[kagaku 2]

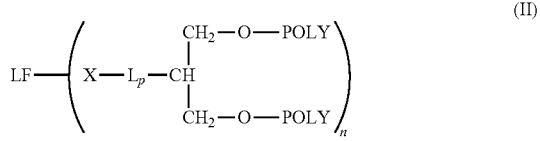

(II)

wherein LF is lactoferrin, X is a linkage generated by reaction of functional groups, L is a linker, POLY is a non-peptide hydrophilic polymer, p is 0 or 1, and n is an integer of 1 to 10;

[4] The complex according to any of [1] to [3], wherein POLY is selected from the group consisting of poly(alkylene glycol), poly(oxyethylated polyol), poly(olefinic alcohol), poly(vinyl pyrrolidone), poly(hydroxyalkyl methacrylamide), poly(hydroxyalkyl methacrylate), poly(saccharide), poly(α-hydroxy acid), poly(vinyl alcohol), polyphosphazene, polyoxazoline, poly(N-acryloyl morpholine), and modified products thereof, copolymers thereof and mixtures thereof;

[5] The complex according to any of [1] to [4], wherein POLY is polyethylene glycol or a modified product thereof;

[6] The complex according to any of [1] to [5], which maintains iron chelate ability of at least 30% of natural lactoferrin;

[7] The complex according to any of [1] to [6], wherein n is an integer of 1 to 5;

[8] A method of producing a biologically active complex of lactoferrin with a branched non-peptide hydrophilic polymer, the method comprising the step of reacting lactoferrin with a branched non-peptide hydrophilic polymer represented by the following formula [III]:

[kagaku 3]

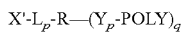

$$X'\text{-}L_p\text{-}R\text{—}(Y_p\text{-POLY})_q \qquad [III]$$

wherein X' is a functional group, L is a linker, R is an aliphatic hydrocarbon group having at least 3 carbon atoms, Y is a heteroatom linkage, POLY is a non-peptide hydrophilic polymer, p is 0 or 1, and q is an integer of 2 to 10, under such conditions as to generate a covalent bond therebetween;

[9] The production method according to [8], wherein lactoferrin and the branched non-peptide hydrophilic polymer are added in a molar ratio of 1:1 to 1:100 to the reaction solution;

[10] The production method according to [8] or [9], wherein the reaction step is carried out under the conditions of pH 4 or more, a temperature of 0 to 40° C. and a time of 1 minute to 24 hours;

[11] A method of purifying a biologically active complex of lactoferrin with a branched non-peptide hydrophilic polymer, the method comprising subjecting a biologically active complex of lactoferrin with a branched non-peptide hydrophilic polymer contained in a sample to:

i) a step of adsorbing the complex onto a cation exchange carrier to concentrate it and then applying the resulting concentrate to a gel filtration carrier, or ii) a step of applying the complex onto a cation exchange gel filtration carrier;

[12] A pharmaceutical composition comprising the biologically active complex of lactoferrin with a branched non-peptide hydrophilic polymer according to any of [1] to [7] and a therapeutically inert base and/or an additive; and

[13] A method of using the biologically active complex of lactoferrin with a branched non-peptide hydrophilic polymer according to any of [1] to [7] for producing a pharmaceutical preparation for treatment or prevention of a disease or a symptom.

The complex of the present invention maintains the ability of lactoferrin to bind to iron, and thus maintains at least the lactoferrin's important bioactivity based on the iron binding ability. Because the complex of the present invention has been endowed with resistance to proteases such as pepsin and trypsin by the binding of a branched non-peptide hydrophilic polymer, the complex has a long in vivo lifetime and can exhibit the bioactivity for a longer time in the body. Further, lactoferrin is made less susceptible to digestion and degradation by pepsin in the stomach as a result of conjugation, and thus, it can reach the intestine sufficiently without performing any further pharmaceutical treatment for dissolution in the intestine.

The complex of the present invention is a complex wherein non-peptide hydrophilic polymers, the number of which is predetermined, have been bound to specific sites of lactoferrin. Thus the complex is uniform in qualities, is advantageous to production control and quality control, and is particularly suitable for use as a pharmaceutical ingredient. That is, lactoferrin can be made further useful as a pharmaceutical ingredient by the complex of the present invention and the method of producing the same. Lactoferrin is extremely safe and has various bioactivities, and is thus further advantageously applicable by the invention as a therapeutic or prophylactic agent for diseases or symptoms for which there is no effective therapeutic agent. For example, the complex of the present invention can be applied to a broader spectrum of applications for lifestyle-related diseases (arteriosclerosis, hypercholesterolemia, hyperlipidemia, hypertension, diabetes mellitus, steatosis etc.), cancers (cancer prevention, secondary prevention of cancer, metastasis suppression, enhancement of anticancer agent action, etc.), autoimmune diseases (dry eye and dry mouth resulting from Sjogren's syndrome, rheumatoid arthritis, malignant rheumatoid arthritis, collagen disease, multiple sclerosis, systemic lupus erythematosus, systemic lupus erythematosus etc.), neuropsychiatric disorders (dementia, Alzheimer's disease, Parkinson's disease, epilepsy, depression, stop-at-home, schizophrenia, various stress-related illnesses etc.), pain relief (enhancing action of opioid such as morphine, cancer-related pain, neuropathic pain, postherpetic pain, fibromyalgia, postoperative pain, glossodynia, cramps, toothache, arthralgia etc.), hepatitis (various types of viral hepatitis, non-alcoholic hepatitis, hepatic cirrhosis etc.), inflammatory bowel diseases (colon ulcer, Crohn's disease etc.), the irritable bowel syndrome, prostatic hyperplasia, pollakiuria, insomnia and constipation. Lactoferrin contained in the complex of the present invention has an antibacterial/antiviral action and an immunity activating action, and thus the complex of the present invention and a pharmaceutical composition containing the same can also be applied to various infections and inflammations based thereon, for example, gastric mucosal infection with *Helicobacter pylori*, periodontal diseases, alveolar pyorrhea, halitosis, oral candidiasis, stomatitis, angular stomatitis, rhinitis, esophagitis, cholecystitis, urinary tract infection, vaginal infection, tinea pedis, acne, herpes group virus infection, senile pneumonia and postoperative infection, and also has an action of enhancing the action of antibiotics. On the other hand, lactoferrin also has an action of bringing about immunological tolerance, so the complex of the present invention and a pharmaceutical composition containing the same can also be applied to allergic diseases such as pollinosis, atopic dermatitis, seborrhea and urticaria. It should be noted that lactoferrin has a potent antioxidant stress action based on the iron chelating action, and the complex of the present invention and a pharmaceutical composition containing the same can also be applied to Wilson's disease, fulminant hepatic failure, anti-aging and rejuvenation of the skin and eye, age-related macular degeneration, diabetic retinopathy, and keratinization suppression and rejuvenation of mucosal epithelial cells.

BEST MODE FOR CARRYING OUT THE INVENTION

Figure 1:
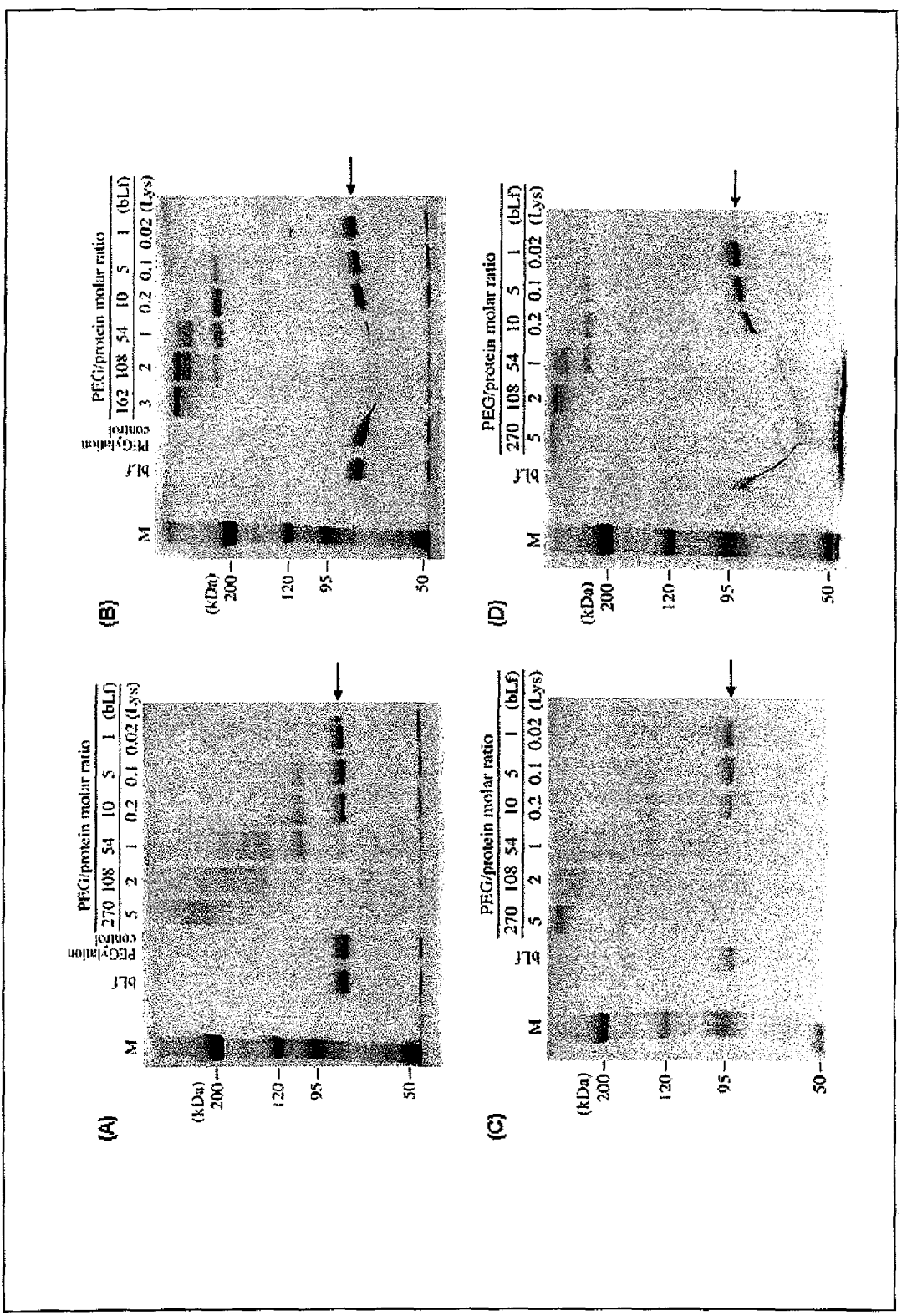
FIG. 1 is a photograph of a gel wherein bovine lactoferrin modified with a branched PEG derivative is analyzed by 7.5% SDS-PAGE and staining with CBB.

The complex of the present invention is a biologically active complex between a branched non-peptide hydrophilic polymer and lactoferrin. Generally, the non-peptide hydrophilic polymer to be bound to lactoferrin to form the complex of the present invention may be a polymer having, at one terminal thereof, a functional group capable of reacting with a functional group of lactoferrin to form a covalent bond therebetween, which polymer is branched (that is, has 2 or more polymer chains), and applicable to the living body or physiologically inert. The term "non-peptide" means that a peptide linkage is not contained, or substantially not contained; that is, a peptide linkage(s) can be contained to such a low extent (for example, about 1 to 5% of the total monomer units constituting the polymer) that the properties of the polymer are not influenced.

Preferably, the complex of the present invention is represented by the following formula [I]:

[kagaku 4]

$$LF\text{-}[X\text{-}L_p\text{-}R\text{—}(Y_p\text{-}POLY)_q]_n \quad \quad [I]$$

or [II]:

[kagaku 5]

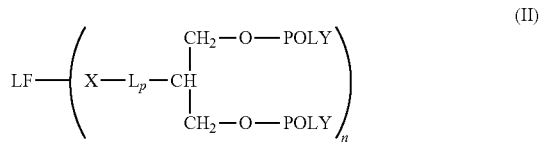

wherein LF is lactoferrin, X is a linkage generated by reaction of functional groups, L is a linker, R is an aliphatic hydrocarbon group having at least 3 carbon atoms, Y is a heteroatom linkage, POLY is a non-peptide hydrophilic polymer, p is 0 or 1, q is an integer of 2 to 10, and n is an integer of 1 to 10.

Preferably, the POLY moiety in the formula is selected from the group consisting of poly(alkylene glycol) (for example, polyethylene glycol (PEG)), poly(oxyethylated polyol), poly(olefinic alcohol), poly(vinyl pyrrolidone), poly (hydroxyalkyl methacrylamide), poly(hydroxyalkyl methacrylate), poly(saccharide), poly(α-hydroxy acid), poly(vinyl alcohol), polyphosphazene, polyoxazoline, poly(N-acryloyl morpholine), and modified products thereof, copolymers thereof (including, for example, copolymers of PEG and polypropylene glycol; terpolymers etc.) and mixtures thereof. Each of the POLY moieties may be linear or branched and/or may have a pedant group and the like.

From the viewpoint of easy availability, the POLY moiety is most preferably PEG or a modified product thereof (for example, a methoxylated product thereof), particularly preferably linear PEG or methoxy PEG.

The number of POLY moieties (q in the formula) can be generally about 2 to 10, preferably about 2 to 6.

X is a linkage generated by the reaction between a functional group (for example, an ε-amino group of lysine) of lactoferrin and a functional group (X' in the formula [III] below; for example, a maleimide group, an aldehyde group, an amino group, an NHS group, and the like) of a branched non-peptide hydrophilic polymer.

Y is a heteroatom linkage such as —O—, —S— or —NH—.

L is a group acting as a linker and is not particularly limited, and like Y, it may or may not be present.

The "lactoferrin" (LF) used in the complex of the present invention may be a naturally occurring or natural-type lactoferrin molecule itself or a recombinant lactoferrin (including lactoferrin modified by partial amino acid replacement) or a functional equivalent of lactoferrin, such as an active fragment of lactoferrin, and is not limited with respect to the presence or the lack of iron ions, the amount of iron ions, the biological species from which lactoferrin is derived, and so on.

In naturally occurring lactoferrin, there are about 44 (human LF) to 54 (bovine LF) lysine residues, but the reactivity of such a residue varies depending on the local environment of the position where the residue is present. According to the method of the present invention, non-peptide hydrophilic polymers are covalently bound with good reproducibility to 1 to 10 functional groups, preferably 1 to 5 functional groups, out of the functional groups possessed by lysine residues of lactoferrin, in the complex. It follows that in the formulae [I] and [II], n is preferably 1 to 5.

The term "biologically active" with respect to the complex of the present invention means that the physiological and/or pharmacological activity of lactoferrin is maintained. Particularly, the complex of the present invention has an iron chelate (binding) ability that is equivalent to that of naturally occurring lactoferrin. Specifically, when the iron binding ability of naturally occurring lactoferrin, as determined by the method described in the Examples described below, is assumed to be 100%, the complex of the present invention maintains at least 30% (for example, about 30% to about 150%, or about 30% to about 120%) iron binding ability. In a preferable embodiment, the complex of the present invention has about 50% to about 100% or more (for example, about 50% to about 150%, or about 50% to about 120%) of the iron binding ability of naturally occurring lactoferrin. When the iron binding ability is measured by the method described in the Examples or a method equivalent thereto, there can be an error of about ±20%.

The complex of the present invention has protease resistance. That is, the complex of the present invention, as compared with naturally occurring lactoferrin, is significantly resistant to digestion with at least pepsin and/or trypsin and chymotrypsin. Preferably, the complex of the present invention has such pepsin resistance that after digestion with pepsin for 20 minutes under the conditions described in the Examples, the lactoferrin remains undigested at a higher degree by about 1.1- to about 2-fold or more (for example, about 2- to about 5-fold) than naturally occurring lactoferrin does.

The complex of the present invention can be produced by reacting functional groups of branched non-peptide hydrophilic polymers with functional groups of lactoferrin, thereby forming covalent bonds therebetween. For example, the branched non-peptide hydrophilic polymers represented by the following formula [III]:

[kagaku 6]

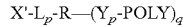

or [IV]:

[kagaku 7]

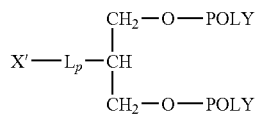

may be used, wherein X' is a functional group, L is a linker, R is an aliphatic hydrocarbon group having at least 3 carbon atoms, Y is a heteroatom linkage, POLY is a non-peptide hydrophilic polymer, p is 0 or 1, and q is an integer of 2 to 10.

X' includes a maleimide group, an aldehyde group, an amino group and an NHS group. L, Y and POLY are the same as described for the complex. Such branched non-peptide hydrophilic polymers can be synthesized by methods known in the art, or a wide variety of such polymers are commercially available. The molecular weight (number-average molecular weight) of the branched non-peptide hydrophilic polymer used in the reaction is generally about 500 to 200,000, preferably 2,000 to 100,000, and particularly preferably 10,000 to 60,000 (Da).

Preferably, lactoferrin and the branched non-peptide hydrophilic polymer are added in a molar ratio of 1:1 to 1:100 to a reaction solution. The molar ratio of lactoferrin to the branched non-peptide hydrophilic polymer is more preferably in the range of 1:3 to 1:60, and most preferably 1:5 to 1:54.

The reaction step is carried out generally under conditions of pH 4 or more, at a temperature of 0 to 40° C. and for a time of 1 minute to 24 hours, preferably under the conditions of pH 6 or more, at a temperature of 4 to 40° C. and for a time of 10 minutes to 24 hours. That is, the pH of the reaction solution is preferably pH 6 or more, and more preferably pH 6 to 9. The reaction time and reaction temperature can be changed while being closely correlated with each other, but generally when the reaction temperature is higher, the time is preferably made shorter, while when the temperature is lower, the time is preferably made longer. For example, under the conditions where the reaction pH is around 7 and the molar ratio of lactoferrin:branched non-peptide hydrophilic polymer is 1:10, the reaction is carried out for about 1 hour at 25° C. or for about 24 hours at 16° C. or 4° C., whereby particularly excellent results (uniform complex etc.) can be obtained. Under the conditions where the molar ratio of lactoferrin: branched non-peptide hydrophilic polymer is 1:1, the reaction is carried out at 25° C. for about 10 minutes or at 16° C. for about 10 minutes to about 40 minutes, or for about 1 hour to about 2 hours at 4° C., whereby particularly excellent results can be obtained.

The complex of the present invention contained in a sample, which was produced as described above, can be easily purified by first adsorbing it onto a cation exchange carrier (resin) such as heparin to concentrate it and then applying the resulting concentrate onto a gel filtration carrier (resin). Specifically, a sample containing the complex is first applied onto a heparin column to adsorb the complex onto the column, followed by eluting the complex with a buffer at a higher salt concentration, to collect an eluent containing the concentrated complex. Then, this eluent can be applied onto a gel filtration column and then desalted, and the buffer in the eluent can be replaced by a desired buffer. If necessary, the eluent can further be concentrated suitably by known methods such as dialysis and ultrafiltration. In another embodiment, the above two steps of concentration and purification, by the cation exchange carrier treatment and the gel filtration carrier treatment, can be effected in one step by using a commercially available cation exchange gel filtration carrier.

Lactoferrin has a wide variety of bioactivities including an antibacterial action, an iron metal metabolism regulating action, a cell growth activating action, a hematopoietic action, an anti-inflammatory action, an antioxidant action, a phagocytosis-promoting action, an antiviral action, a bifidobacteria growth promoting action, an anticancer action, a cancer metastasis inhibiting action, a translocation inhibiting action, a lipid metabolism improving action, an analgesic action and an antistress action, and enables, by these actions, the treatment (including amelioration) and prevention of many diseases, or symptoms thereof, including lifestyle-related diseases (for example, hypercholesterolemia, hyperlipidemia, and the like), pain control (cancerous pain, neuropathic pain, and the like), collagen diseases (dry eye and dry mouth resulting from Sjogren's syndrome, rheumatic arthritis, and the like), periodontal diseases and hepatitis C. The complex of the present invention sufficiently has the bioactivity of lactoferrin and can thus be formed into a pharmaceutical composition by blending the complex with a therapeutically inert base and/or an additive. For the sake of convenience, the pharmaceutical preparation or pharmaceutical composition referred to in the present invention encompasses those whose administration object includes not only humans but also animals (that is, veterinary medicines etc.). Various components which can be contained in such pharmaceutical compositions and dosage forms are well known to those skilled in the art. The effective dose of the pharmaceutical composition containing the complex of the present invention varies depending on the dosage form or on the type or degree of diseases or symptoms to be treated or prevented, or on the condition of an object to whom the composition is administered, and can be selected suitably in consideration of the known effective dose of lactoferrin as a guide. Generally, the dose may be significantly reduced (for example, $\frac{1}{2}$ to $\frac{1}{20}$ in terms of the amount of lactoferrin) relative to the known effective dose of lactoferrin, and when used in the same dose as the known dose, the frequency of administration can be reduced.

EXAMPLES

1. Preparation of Pegylated Lactoferrin

Complexes with lactoferrin were prepared by using various PEG derivatives.

As lactoferrin, bovine lactoferrin (manufactured by Maray Golvan Co., Ltd.) was used. The targets of pegylation were lysine ε-amino groups (there are 54 groups per bovine lactoferrin molecule) and the N-terminal α-amino group of lactoferrin.

As the PEG derivatives, the following 4 types of branched PEG derivatives (Examples) and 3 types of linear PEG derivatives (Comparative Examples) were used.

TABLE 1

Used PEG Derivatives

| | | PEG Derivatives |
|---|---|---|
| Branched | 1 | mPEG2-NHS (MW = 10 kDa) manufactured by Nektar |
| | 2 | mPEG2-NHS (MW = 40 kDa) manufactured by Nektar |
| | 3 | SUNBRIGHT GL2-200GS2 (MW = 20 kDa) manufactured by NOF Corporation |
| | 4 | SUNBRIGHT GL2-400GS2 (MW = 40 kDa) manufactured by NOF Corporation |
| Linear | 5 | Methoxy polyethylene glycol Succinimidyl succinate (MW = 5 kDa) manufactured by Sigma |
| | 6 | SUNBRIGHT ME-200TR (MW = 20 kDa) manufactured by NOF Corporation |
| | 7 | SUNBRIGHT MEGC-30TS (MW = 30 kDa) manufactured by NOF Corporation |

A predetermined amount of PEG derivative was mixed with 0.5 mg (6.25 μM) of bovine lactoferrin (bLf) in PBS (pH 7.4) and subjected to coupling reaction at 25° C. for 1 hour in a final volume of 1 ml. The final concentration of lactoferrin was 0.5 mg/ml. The ratio of PEG derivative and bLF, in terms of the molar ratio of PEG derivative/lysil group, was varied in the range of 0.02 to 5, or the bLf:PEG derivative molar ratio was varied from 1:1 to 1:270 (corresponding to a PEG derivative concentration of 6.25 μM to 1.69 mM).

Figure 2:
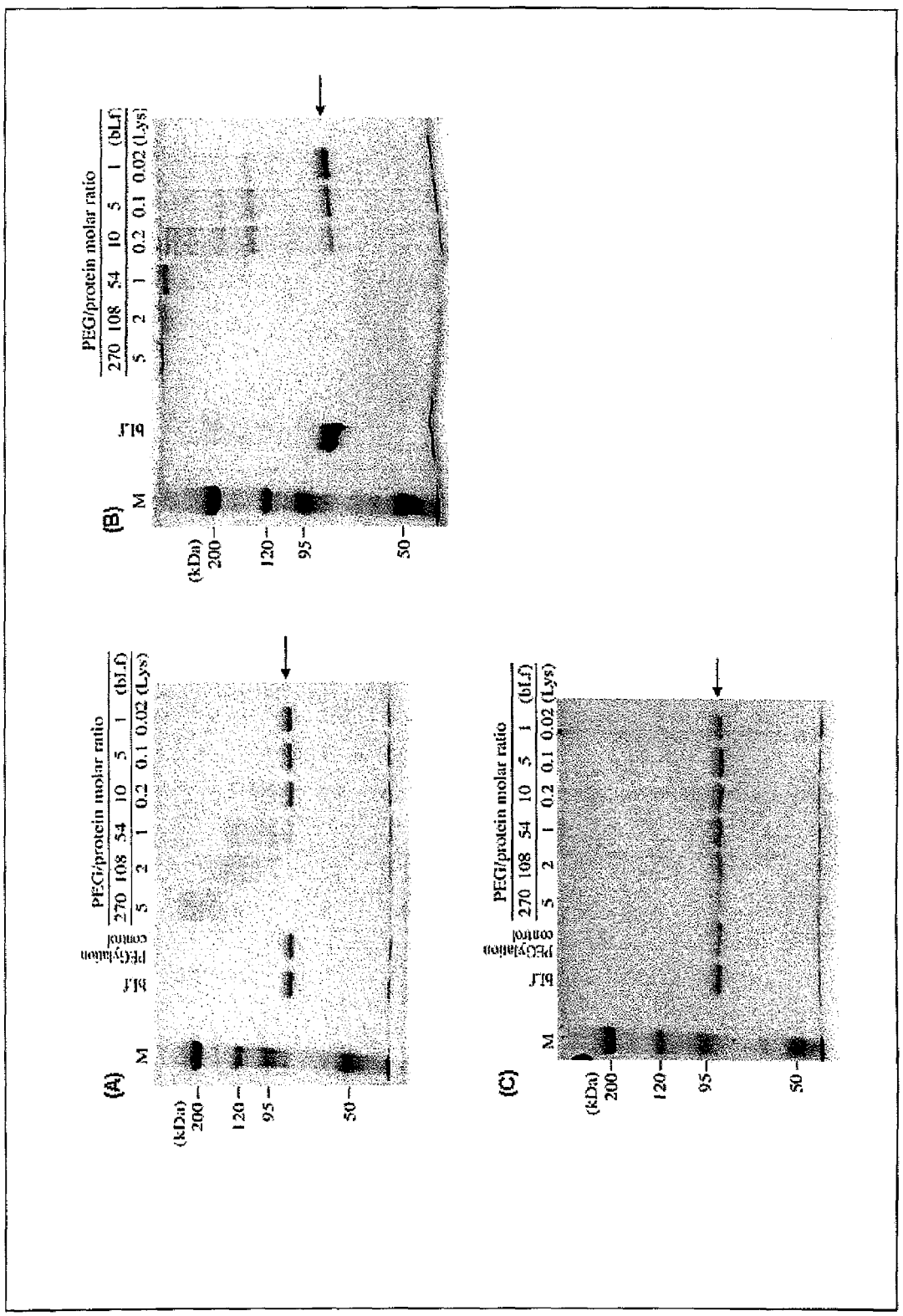
FIG. 2 is a photograph of a gel wherein bovine lactoferrin modified with a linear PEG derivative is analyzed by 7.5% SDS-PAGE and staining with CBB.

The product of the coupling reaction was evaluated by staining it with Coomassie Brilliant Blue (CBB) after 7.5% SDS-PAGE. The results are shown in FIGS. 1 and 2. In FIGS. 1 and 2, bands shown by an arrow indicate unmodified bovine lactoferrin.

FIG. 1 is a photograph of a gel wherein bovine lactoferrin modified with a branched PEG derivative was analyzed by 7.5% SDS-PAGE and CBB staining. Panels A to D show the results of reaction products of PEG derivatives 1 to 4, respectively, shown in Table 1. When the coupling reaction with branched PEG derivatives was carried out, it was observed that formed pegylated lactoferrin tended to increase depending on the numbers of moles of the PEG derivatives, and by the reaction under the conditions where the molar ratio of bLf:PEG derivative is 1:5 to 1:54 (concentration of the PEG derivative, 31.25 to 337.5 μM), lactoferrin complexes modified specifically with the PEG derivatives (sharp bands) were formed (FIG. 1, panels A to D). From the molecular weight by electrophoresis, it was estimated that regardless of the molecular weight of the PEG derivative, these pegylated lactoferrins were uniformly modified with about 1 to 4 molecules of PEG per molecule of bLF.

FIG. 2 is a photograph showing the results of similar modification of bovine lactoferrin with linear PEG derivatives. Panels A to C show reaction products of PEG derivatives 5 to 7, respectively, shown in Table 1. It was observed that in the coupling reaction with the linear PEG derivatives, as is the reaction with the branched PEG derivatives, the reaction proceeds depending on the number of moles of the PEG derivatives, and in the reaction of the PEG derivatives 5 (panel A) and 6 (panel B), heterogeneous lactoferrin complexes (smear broad bands) modified with several to numerous PEG molecules were formed. The PEG derivative 7 (panel C) was poor in reactivity so that pegylated lactoferrin could not be confirmed with CBB staining. When the linear PEG derivatives were used, their specificity to the reaction was low even in the case where the complexes were formed, and therefore, formation of the reaction-specific pegylated lactoferrin was not recognized in any reactions.

2. Examination of Reaction pH

In a similar experiment as described above, bovine lactoferrin and PEG derivatives 2 to 4 were used and subjected to coupling reaction at varying pH in the range of 4 to 9 in the coupling reaction solution for pegylation. The buffer solutions used were an acetate buffer for pH 4 to 5, a phosphate buffer for pH 6 to 8, and a borate buffer for pH 9. Other conditions were that the final concentration of bovine lactoferrin was 0.5 mg/ml, the reaction temperature was 25° C., and the reaction time was 1 hour, and the molar ratio of bovine lactoferrin:PEG derivative was 1:54 (concentration of the PEG derivative, 337.5 µM) or 1:10 (concentration of the PEG derivative, 62.5 µM). After the reaction, the reaction products were analyzed by 7.5% SDS-PAGE and CBB staining.

Figure 3:
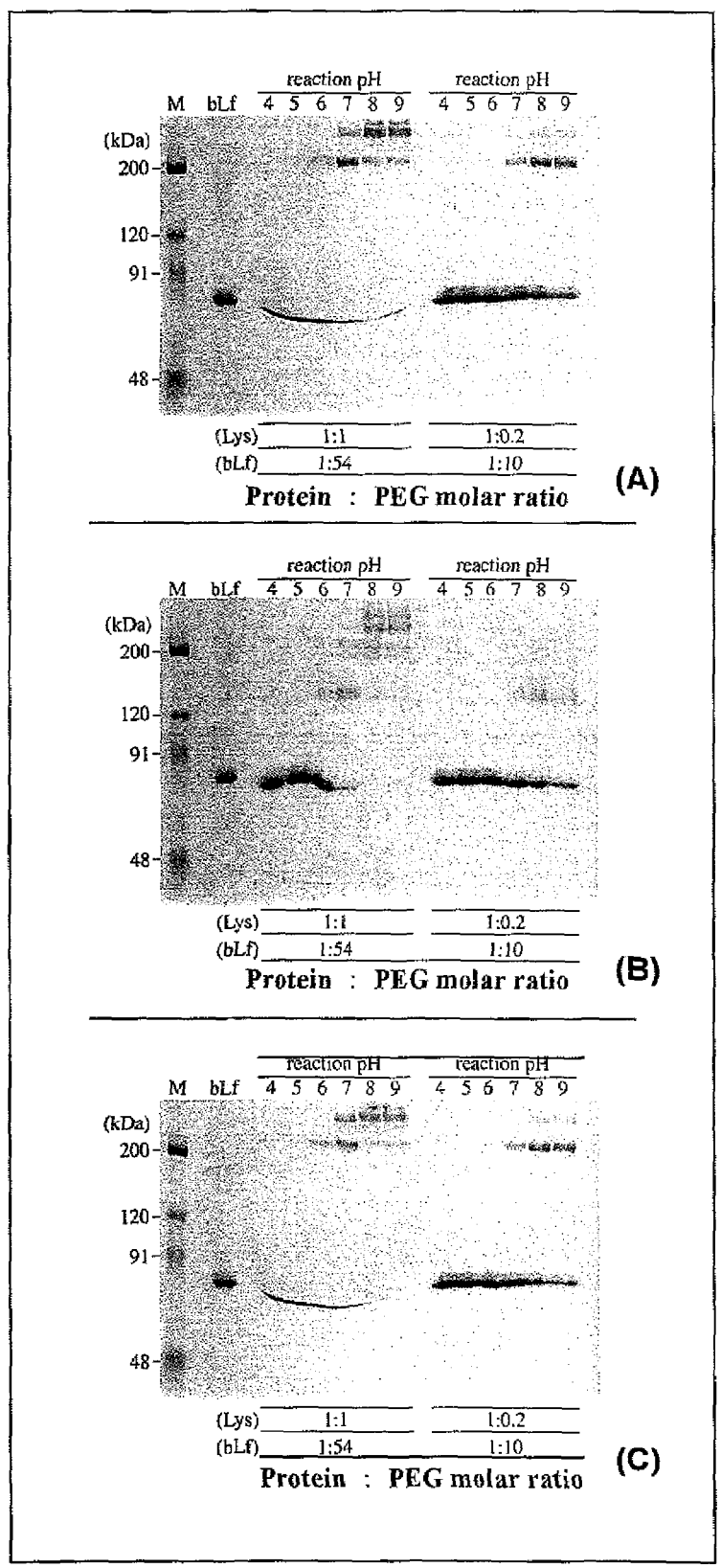
FIG. 3 is a photograph of a gel wherein the formation of a complex of bovine lactoferrin with a branched PEG derivative is analyzed under various pH conditions.

The results are shown in FIG. 3. When any of PEG derivatives 2 to 4 (corresponding to panels A to C, respectively) was used, reaction-specific pegylated lactoferrin formation was confirmed at pH 6 or more. The coupling reaction was confirmed to proceed well in the reaction solution under the condition of pH 6 to 9, and under an alkaline condition the reaction was particularly promoted. On the other hand, the pegylation reaction hardly occurred in the reaction solution under an acidic condition at pH 5 or less.

3. Examination of Reaction Temperature and Time

In a similar experiment as described above, bovine lactoferrin and PEG derivatives 2, 3 and 4 were used and subjected to coupling reaction for pegylation at a reaction temperature of 25° C., 16° C. or 4° C. for a varying reaction time. Other conditions are that the final concentration of bovine lactoferrin was 0.5 mg/ml, the reaction buffer was PBS, pH 7.4, and the molar ratio of bovine lactoferrin:PEG derivative was 1:54 (concentration of the PEG derivative, 337.5 µM) or 1:10 (concentration of the PEG derivative, 62.5 µM). After the reaction, the reaction products were analyzed by 7.5% SDS-PAGE and CBB staining.

Figure 4:
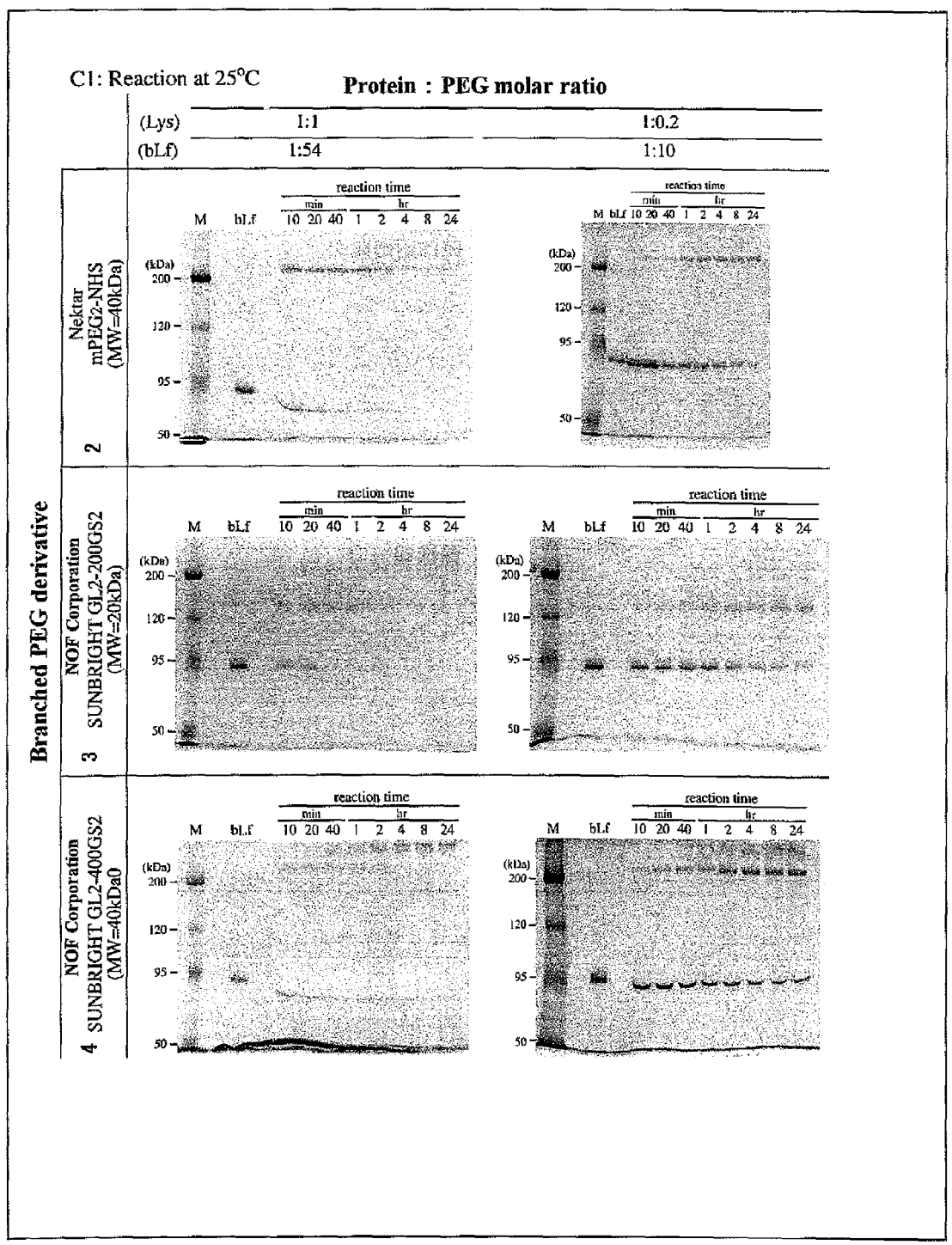
FIG. 4 is a photograph of a gel wherein the formation of a complex of bovine lactoferrin with a branched PEG derivative is analyzed at 25° C. under various reaction time conditions.
Figure 5:
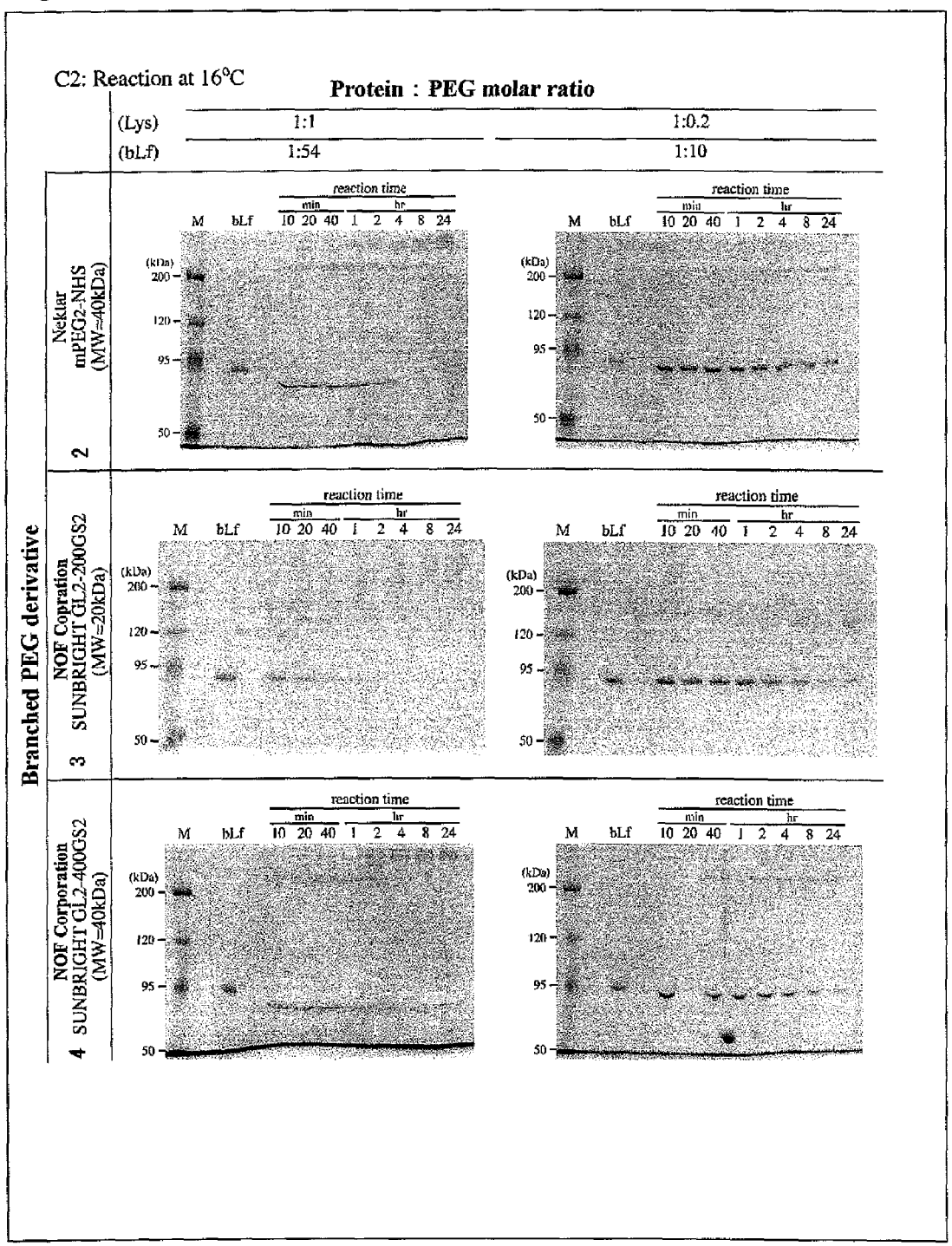
FIG. 5 is a photograph of a gel wherein the formation of a complex of bovine lactoferrin with a branched PEG derivative is analyzed at 16° C. under various reaction time conditions.
Figure 6:
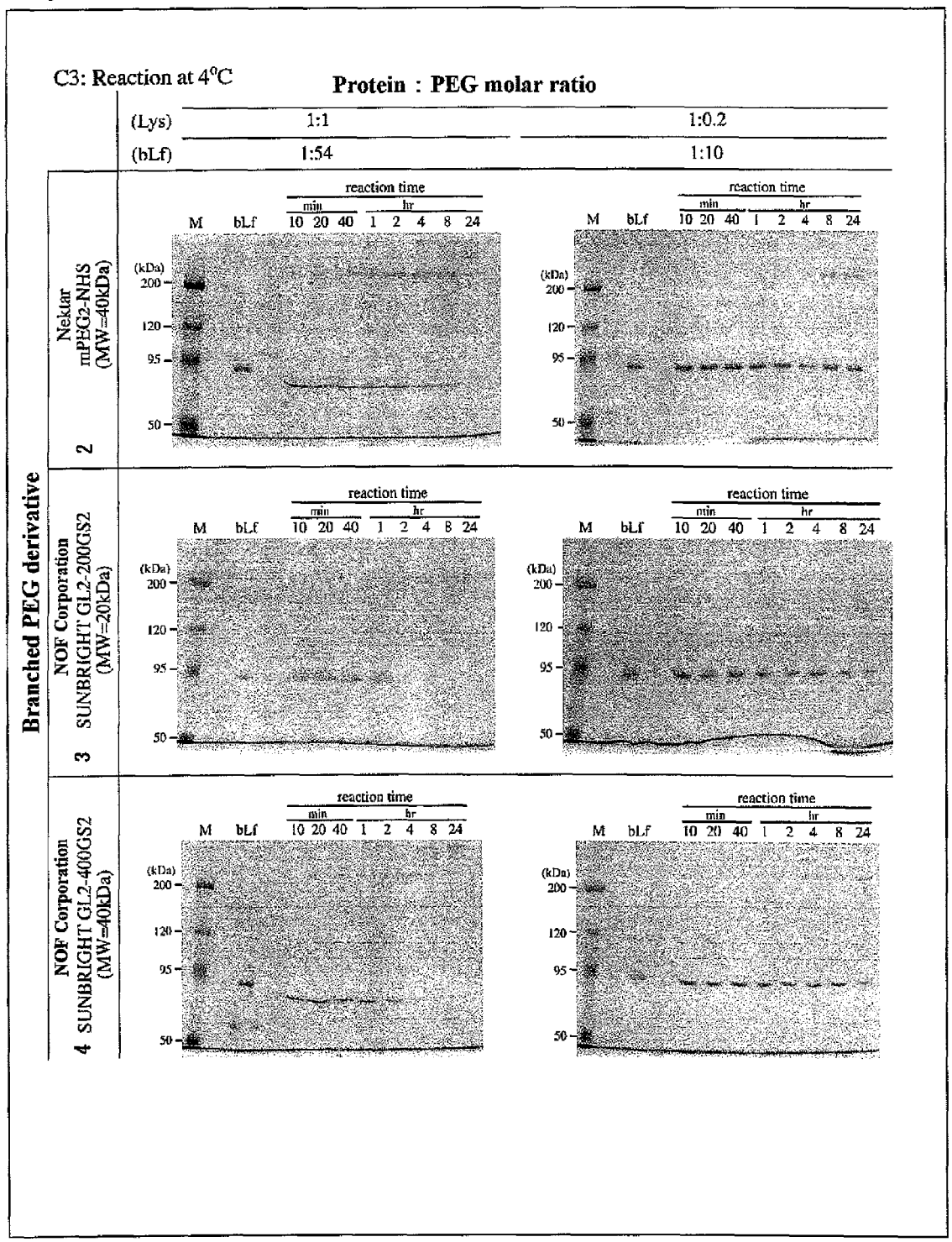
FIG. 6 is a photograph of a gel wherein the formation of a complex of bovine lactoferrin with a branched PEG derivative is analyzed at 4° C. under various reaction time conditions.

The results are shown in FIGS. 4 to 6. It was revealed that when any of the PEG derivatives 2, 3 and 4 (corresponding respectively to FIGS. 4, 5 and 6) was used, the pegylation reaction occurred at any reaction temperatures of 4 to 25° C., that the reaction occurred more easily as the temperature was increased, and that formation of pegylated lactoferrins of higher molecular-weight modified with a large number of PEG derivatives was increased with prolonged reaction time.

Specifically, it was confirmed that when the reaction was carried out at 25° C. under the condition where the molar ratio of bLf:PEG derivative was 1:54 (concentration of the PEG derivative, 337.5 µM), pegylated lactoferrin was formed for both of the 20- and 40-kDa PEG derivatives from a reaction time of 10 minutes, and that, as the reaction time was increased, reaction-specific lactoferrin modified with 1 to 4 molecules of PEG tended to decrease while a higher molecular-weight pegylated lactoferrin tended to be formed. On the other hand, when the reaction was carried out under the condition where the molar ratio of bLf:PEG derivative was 1:10 (concentration of the PEG derivative, 62.5 µM), pegylated lactoferrin was formed from a reaction time of 10 minutes, and the reaction-specific pegylated lactoferrin was increased up to 24 hours, and from 2 hours, high molecular-weight pegylated lactoferrin was also increased (FIG. 4).

It was confirmed that when the reaction was carried out at 16° C. under the condition where the molar ratio of bLf:PEG derivative was 1:54 (concentration of the PEG derivative, 337.5 µM), pegylated lactoferrin was formed for both of the 20- and 40-kDa PEG derivatives from a reaction time of 10 minutes, that reaction-specific lactoferrin modified with 1 to 4 molecules of PEG was formed with a peak at the reaction time of 1 hour, and that, as the reaction time was increased, high molecular-weight pegylated lactoferrin further modified with PEG tended to be formed. On the other hand, it was confirmed that when the reaction was carried out under the condition where the molar ratio of bLf:PEG derivative was 1:10 (concentration of the PEG derivative, 62.5 µM), pegylated lactoferrin was formed from a reaction time of 40 minutes, and that the reaction-specific pegylated lactoferrin tended to increase up to 24 hours (FIG. 5).

It was observed that when the reaction was carried out at 4° C. under the condition where the molar ratio of bLf:PEG derivative was 1:54 (concentration of the PEG derivative, 337.5 µM), pegylated lactoferrin was formed for both of the 20- and 40-kDa PEG derivatives from a reaction time of 10 minutes, that reaction-specific lactoferrin modified with 1 to 4 molecules of PEG was formed with a peak at the reaction time of 4 hours, and that, as the reaction time was increased, high molecular-weight pegylated lactoferrin further modified with a large number of PEG molecules tended to be formed. On the other hand, it was confirmed that when the reaction was carried out under the condition where the molar ratio of bLf:PEG derivative was 1:10 (concentration of the PEG derivative, 62.5 µM), pegylated lactoferrin was formed from a reaction time of 2 hours, and that the reaction-specific pegylated lactoferrin tended to gradually increase up to 24 hours (FIG. 6).

Accordingly, it was confirmed that an excellent coupling reaction occurred at a reaction temperature of 4° C. or more.

4. Preparation of Pegylated Human Lactoferrin

Human lactoferrin (hLf) used in pegylation was purchased from SIGMA (SIGMA, L0520). The targets of pegylation were lysine ε-amino groups (44 groups per protein molecule) and the N-terminal α-amino group of lactoferrin. The PEG derivatives used were 3 types of branched PEG derivatives (PEG derivatives 2 to 4 in Table 1). The coupling reaction was carried out at a final lactoferrin concentration of 0.5 mg/ml at 25° C. for 1 hour in PBS (pH 7.4) in a final volume of 1 ml. The mixing ratio of the PEG derivatives to 0.5 mg (6.25 µM) human lactoferrin (hLf), in terms of the PEG derivative/lysil group, was varied in the range of 0.02 to 5, or the hLf:PEG derivative molar ratio was varied from 1:1 to 1:220 (corresponding to a PEG derivative concentration of 6.25 µM to 1.38 mM). The reaction products were evaluated by 7.5% SDS-PAGE and CBB staining.

Figure 7:
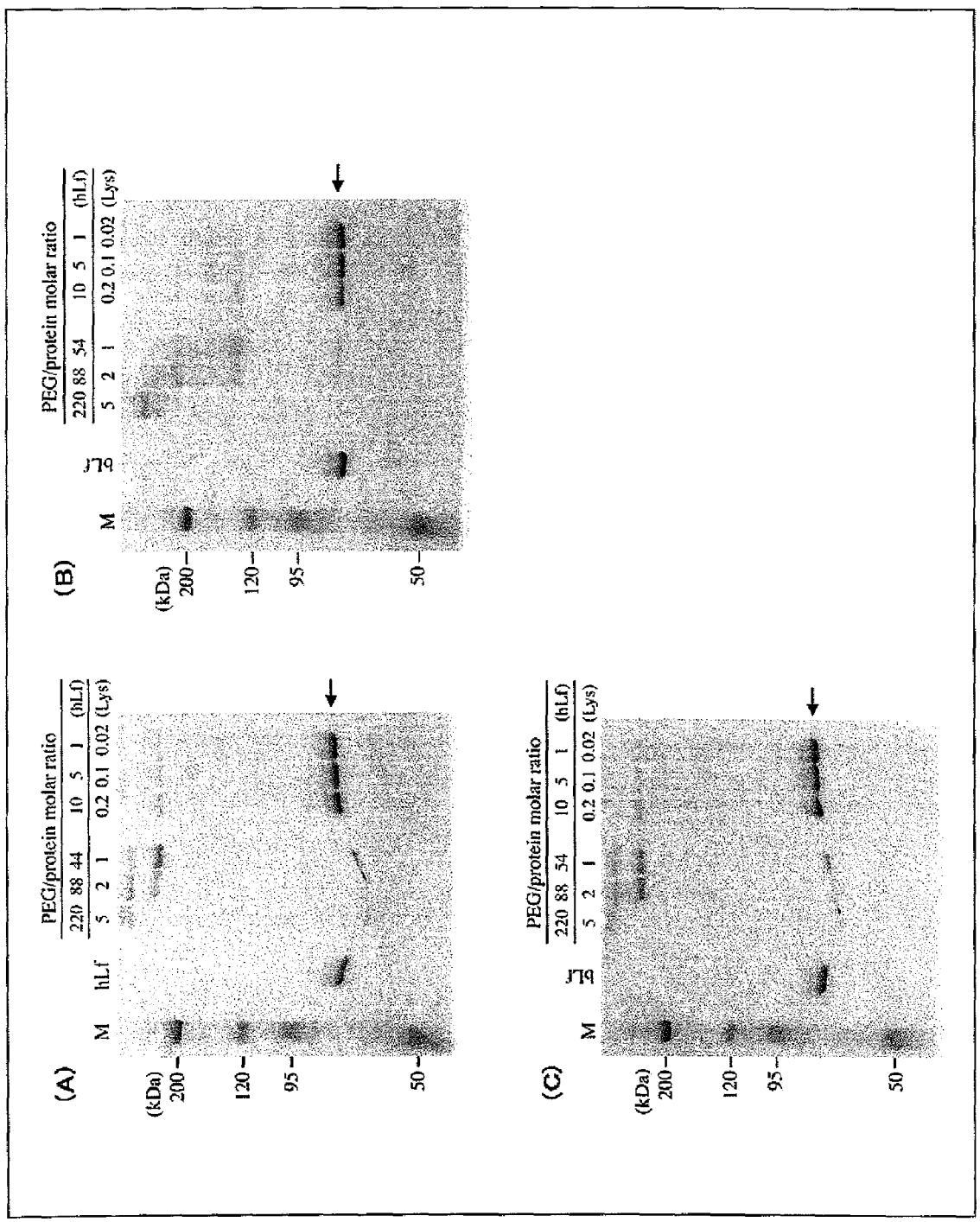
FIG. 7 is a photograph of a gel wherein human lactoferrin modified with a branched PEG derivative is analyzed by 7.5% SDS-PAGE.

The results are shown in FIG. 7. The band shown by an arrow indicates unmodified human lactoferrin. Panels A to C show the results when PEG derivatives 2 to 4, respectively, were used. These coupling reactions showed the same tendency as in the cases where bovine lactoferrin was used. That is, the reaction proceeded depending on the number of moles of the PEG derivative to form lactoferrin modified with several to numerous PEG derivatives, and when hLf and PEG derivative were reacted under the condition where the molar ratio of hLf:PEG derivative was 1:1 to 1:88, particularly around 1:10, specific pegylated lactoferrin was formed. From the molecular weight based on electrophoresis, it was estimated that regardless of the molecular weight of the PEG derivative, the pegylated lactoferrin was modified with about 1 to 4 molecules of PEG.

5. Purification of Pegylated Lactoferrin

By combining a heparin column with a gel filtration column, the uncoupled PEG derivative and the uncoupled lactoferrin in a pegylated bovine lactoferrin reaction solution were separated to purify the pegylated lactoferrin.

The PEG derivatives 3 and 4 in Table 1 were used to prepare 100 ml of a reaction solution in which bLf (0.5 mg/ml) and the PEG derivative were mixed in a molar ratio of 1:10, followed by reaction at 25° C. at pH 7.4 for 1 hour. 96 ml of this reaction solution (corresponding to 48 mg protein) was used as a sample. First, the reaction product was adsorbed onto a HiTrap Heparin HP column (column size 5 ml, Amersham Bioscience). Elution of pegylated lactoferrin was carried out with AKTA explorer 10S (Amersham Bioscience). Using 10 mM sodium phosphate buffer, pH 7.6, as the buffer solution and 10 mM sodium phosphate buffer, pH 7.6, containing 1 M NaCl as the elution buffer, the adsorbed substance was elated by increasing the salt concentration in a linear gradient of a 20-column volume at a flow rate of 1 ml/min., to recover pegylated lactoferrin fractions. These pegylated lactoferrin fractions were dialyzed overnight against PBS at 10° C. and then concentrated to a volume of about 1 ml with CENTRIPLUS YM-50 (MILLIPORE). In final purification, the concentrate thus obtained was applied onto a Superdex 200 10/300GL (Amersham Bioscience) column and eluted at a flow rate of 0.5 ml/min with a 1.5-column volume of 50 mM sodium phosphate buffer, pH 7.0, containing 150 mM NaCl, to recover pegylated lactoferrin fractions. The resulting purified samples (pegylated lactoferrins obtained using the PEG derivatives 3 and 4 are respectively referred to as 20k-PEG-bLf and 40k-PEG-bLf) were confirmed by silver staining after 7.5% SDS-PAGE.

Figure 8:
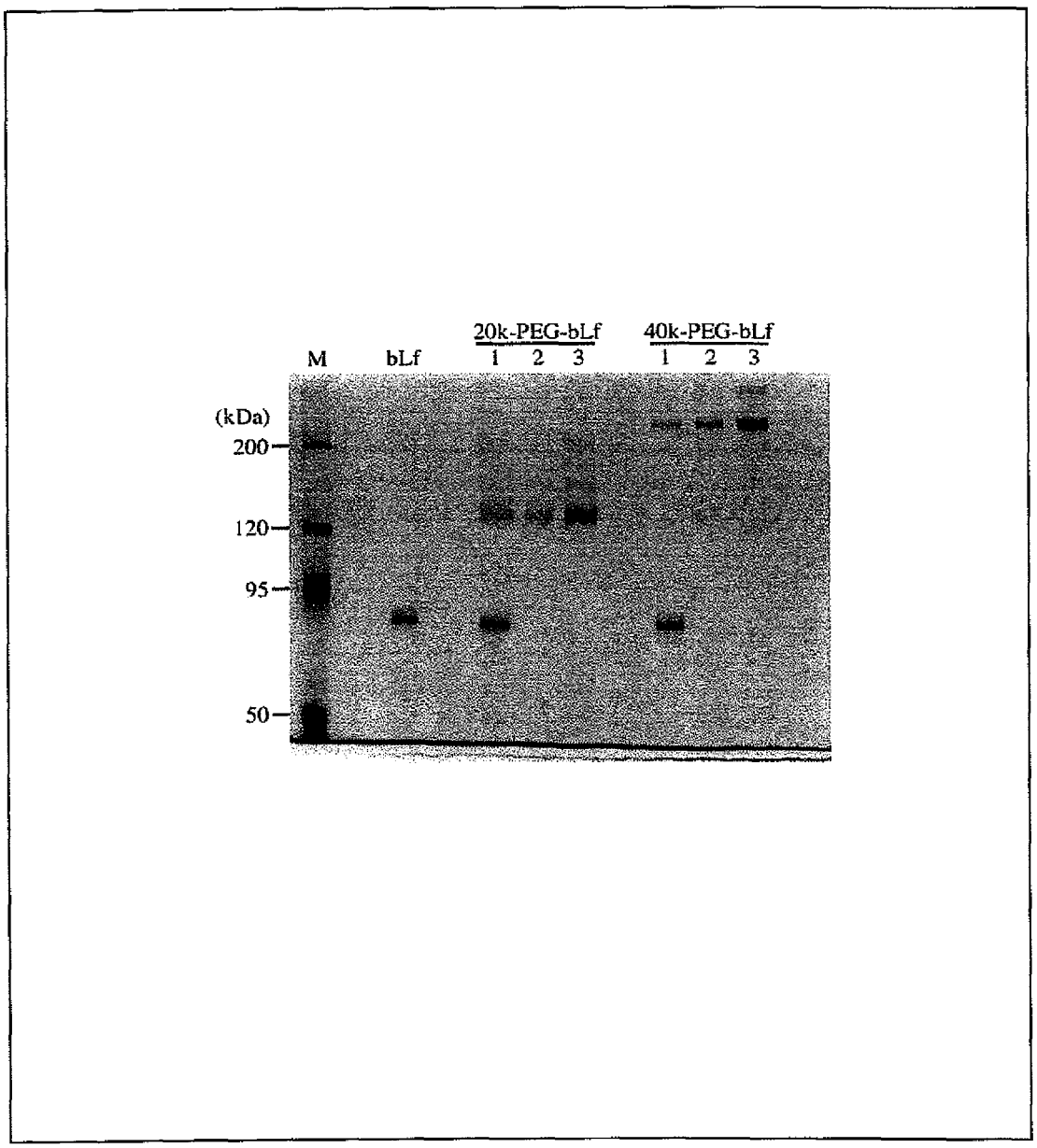
FIG. 8 is a photograph of a gel wherein pegylated bovine lactoferrin after purification though a heparin column and a gel filtration column is analyzed by 7.5% SDS-PAGE.

The results are shown in FIG. 8. In FIG. 8, lane 1 is the pegylated reaction solution, lane 2 is the protein purified with the heparin column, and lane 3 is the protein purified with the gel filtration column. Accordingly, it was confirmed that by using the heparin column and gel filtration column, only the pegylated lactoferrin was purified from the coupling reaction solution.

6. Staining of Purified Pegylated Lactoferrin with Barium Iodide

A pegylated protein is stained specifically with barium iodide (Kurfurst M M, Anal Biochem, 200, 244-248 (1992); Balion P. et al., Bioconjug Chem, 12, 195-202 (2001)). To confirm whether the pegylated bLf produced and purified in the experiment in Section 5 above was certainly modified with PEG, staining with barium iodide was carried out.

Each of the samples shown below was subjected to 7.5% SDS-PAGE, and then the gel was washed with deionized water for 15 minutes, shaken for 10 minutes in 5% (w/v) barium chloride solution, and then washed with deionized water 3 times each for 3 minutes. Then, the gel was shaken in 0.1 N Titrisol iodine solution (MERCK, Germany) for 10 minutes, thereby staining the pegylated lactoferrin. The gel thus stained with the Titrisol iodine solution was washed with water and completely decolorized, followed by staining with CBB. The results are shown in FIG. 9.

Figure 9:
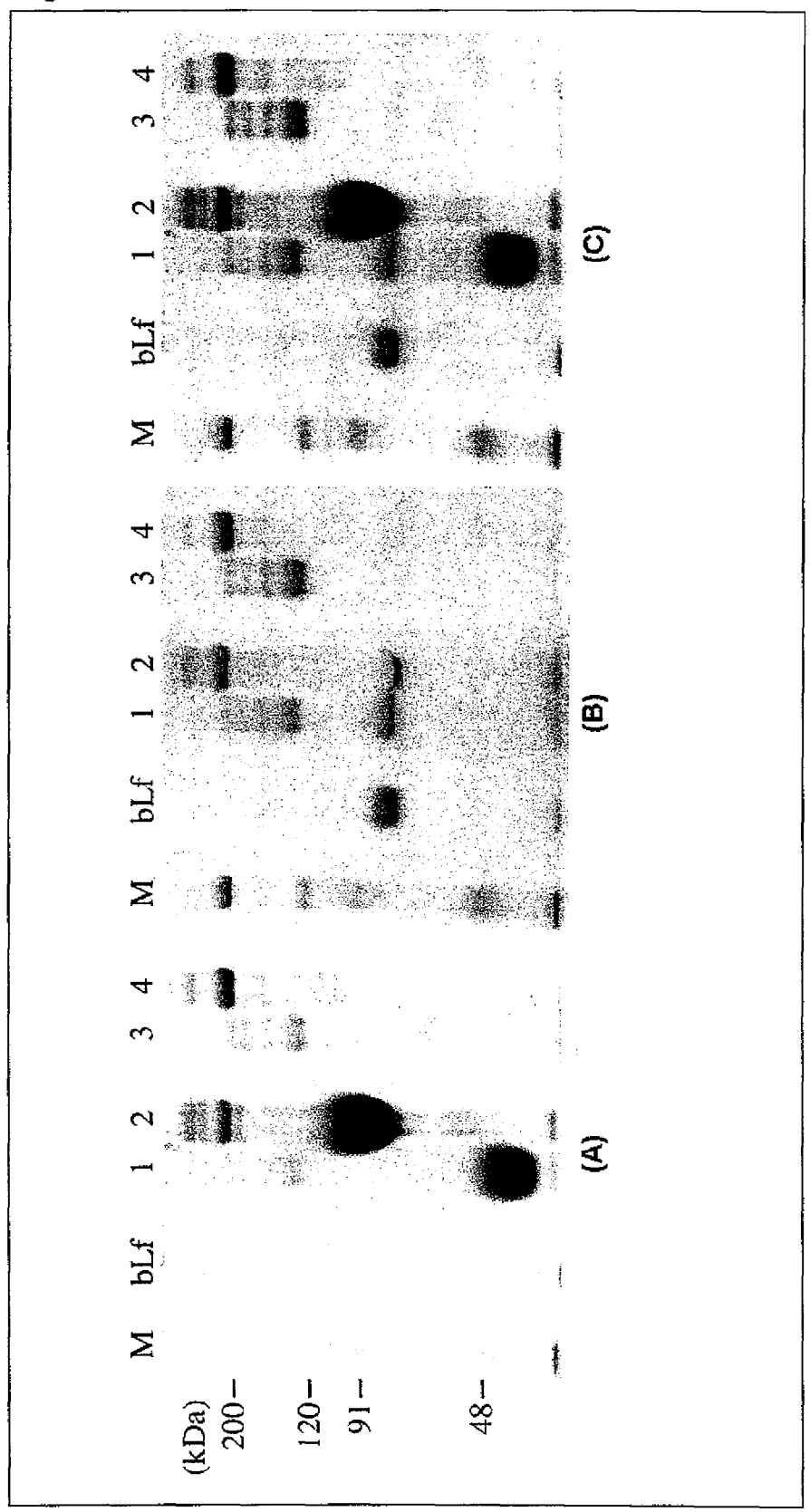
FIG. 9 is a photograph of a gel wherein the pegylation of purified pegylated bLf is examined by staining with barium iodide.

In FIG. 9, panel A shows a barium iodide-stained image, panel B shows a CBB-stained image, and panel C shows an image obtained by overlapping the barium iodide-stained image with the CBB-stained image. The sample in each lane is as follows: "bLf"=unmodified bovine lactoferrin, "1"=the coupling reaction solution using the PEG derivative 3, "2"=the coupling reaction solution using the PEG derivative 4, "3"=purified pegylated bLf (20k-PEG-bLf), "4"=purified pegylated bLf (40k-PEG-bLf). Lane M is a marker.

In the barium iodide-stained images (panels A and C), the dark stained bands in lane 1 (molecular weight, about 45 kDa) and lane 2 (molecular weight, about 90 kDa) are bands of the unreacted PEG derivatives. That is, it can be seen that in SDS-PAGE, the PEG derivative reagent having a number-average molecular weight of about 20 kDa was electrophoresed to a position of apparently about 45 kDa, and the PEG derivative reagent having a number-average molecular weight of about 40 kDa was electrophoresed to a position of apparently about 90 kDa. The protein not pegylated was not stained (lanes bLf, 1 and 2; molecular weight, about 80 kDa). On the other hand, it was confirmed that purified pegylated lactoferrin was stained in barium iodide staining and CBB staining (lanes 1 and 3, molecular weight about 140 kDa; lanes 2 and 4, molecular weight about 240 kDa). Because the purified protein was stained with barium iodide, it was confirmed that the purified protein had been certainly modified with PEG.

7. Evaluation of Resistance to Pepsin and Trypsin Digestion

The purified pegylated bLfs (20k-PEG-bLf and 40k-PEG-bLf) obtained in the experiments described in the above Section 5 were digested with pepsin or trypsin under the following conditions, and their digestion was examined by comparison with digestion of unmodified bLf.

For pepsin digestion, pepsin (derived from swine stomach, code No. 165-18713, manufactured by Wako Pure Chemical Industries, Ltd.) was added at a final concentration of 18.75 ng/ml to 10 μg of each of the purified unmodified bLfs, 20k-PEG-bLf and 40k-PEG-bLf, and reacted in 0.01 M HCl at 37° C. 20, 40, 60, 80 and 100 minutes after the reaction was initiated, an aliquot (corresponding to 1.25 μg of each protein) was sampled with a pipette and mixed with an equal volume of ice-cold 2× Sample buffer (100 mM Tris-HCl (pH 6.8), 4% SDS, 20% glycerol, a dye (BPB)), thereby terminating the enzyme reaction.

For trypsin digestion, trypsin (derived from bovine spleen, code No. 204-13951, manufactured by Wako Pure Chemical Industries, Ltd.) was added at a final concentration of 20 μg/ml to 10 μg of each of the purified bLfs, 20k-PEG-bLf and 40k-PEG-bLf, and reacted at 37° C. in 50 mM Tris-HCl (pH 6.8), 0.1 M NaCl, and 2 mM $CaCl_2$. 10, 20, 30, 40, 50 and 60 minutes after the reaction was initiated, an aliquot (corresponding to 1.25 μg of each protein) was sampled with a pipette and mixed with an equal volume of ice-cold 2× Sample buffer, thereby terminating the enzyme reaction. The results are shown in FIGS. 10 to 12.

Figure 10:
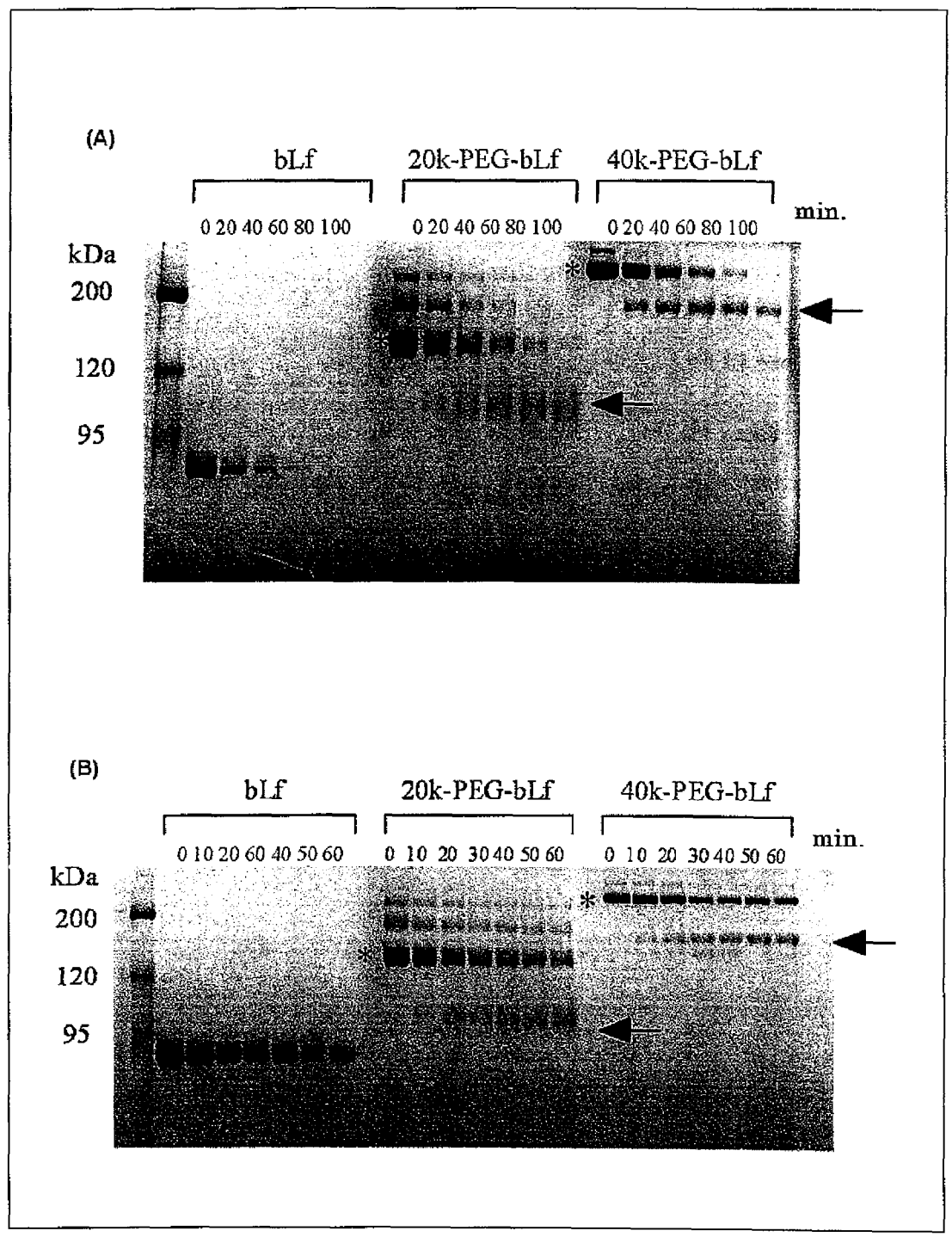
FIG. 10 is a photograph of a gel wherein unmodified lactoferrin and purified pegylated lactoferrin after digestion with pepsin (panel A) or trypsin (panel B) are analyzed by 10% SDS-PAGE.

FIG. 10 is a photograph of a gel stained with CBB after electrophoresis of each sample on 10% (unreduced) SDS-PAGE. In FIG. 10, panels A and B show the results of digestion with pepsin and trypsin, respectively. A band of the purified pegylated lactoferrin is shown by a mark *, and a band of fragmented pegylated lactoferrin is shown by an arrow. By digestion with pepsin (panel A) or trypsin (panel B), the unmodified bLf was rapidly degraded into a lower molecule, but 20k-PEG-bLf and 40k-PEG-bLf were digested in a limited way, and the fragmented band shown by an arrow was observed. From this result, it can be seen that pegylated LF, as compared with unmodified bLf, is reluctant to undergo the action of pepsin and trypsin.

Figure 11:
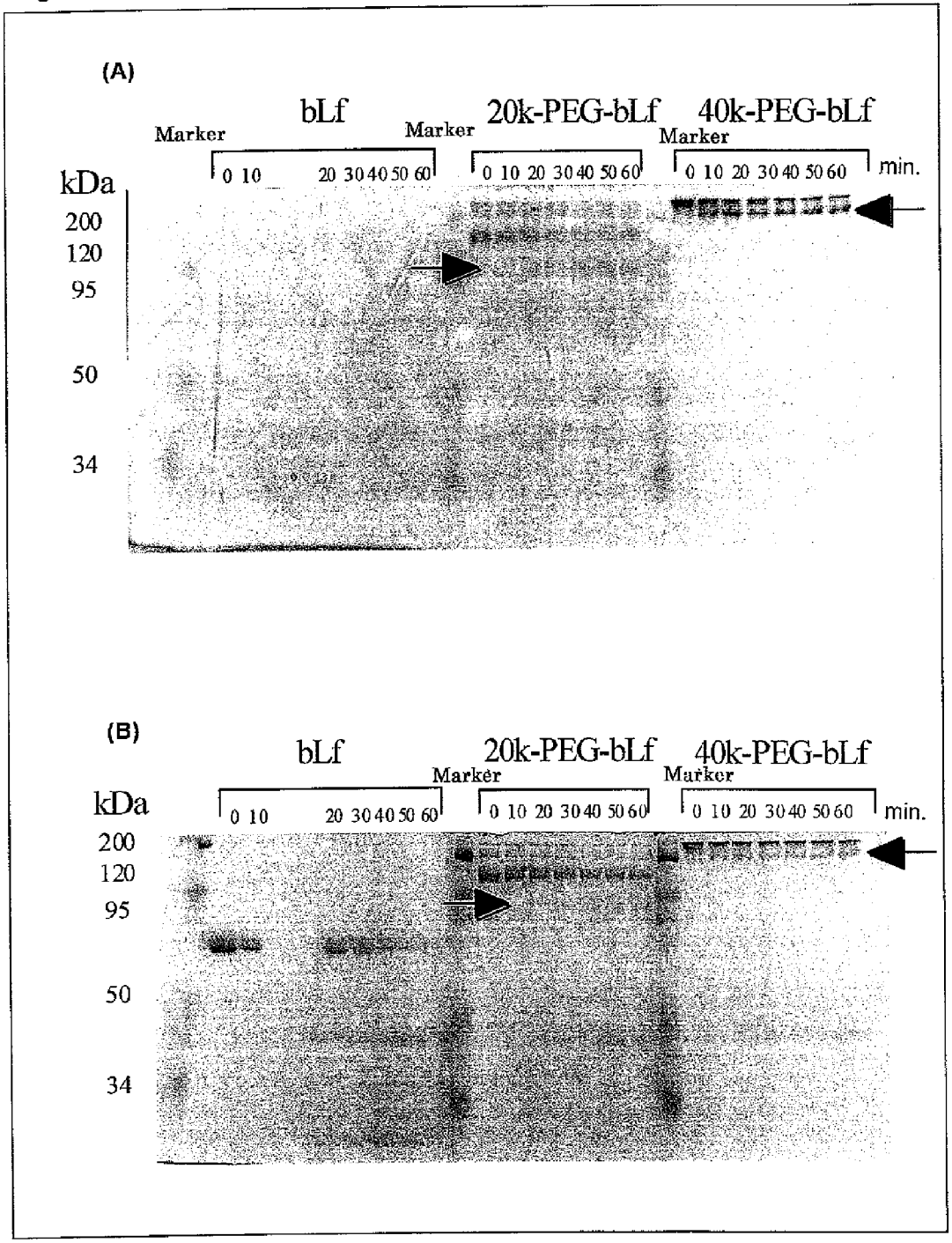
FIG. 11 is a photograph of a gel wherein unmodified lactoferrin and purified pegylated lactoferrin after digestion with trypsin are analyzed by 10% SDS-PAGE.

FIG. 11 shows the results of analysis of the trypsin digests by 12% SDS-PAGE and subsequent staining with barium iodide (panel A) or staining with CBB (panel B). The CBB-stained bands indicated by an arrow in panel B and FIG. 8 were stained with barium iodide (panel A), and thus it can be seen that the bands shown by the arrow are pegylated lactoferrin fragments, and they became resistant to trypsin digestion by pegylation.

Figure 12:
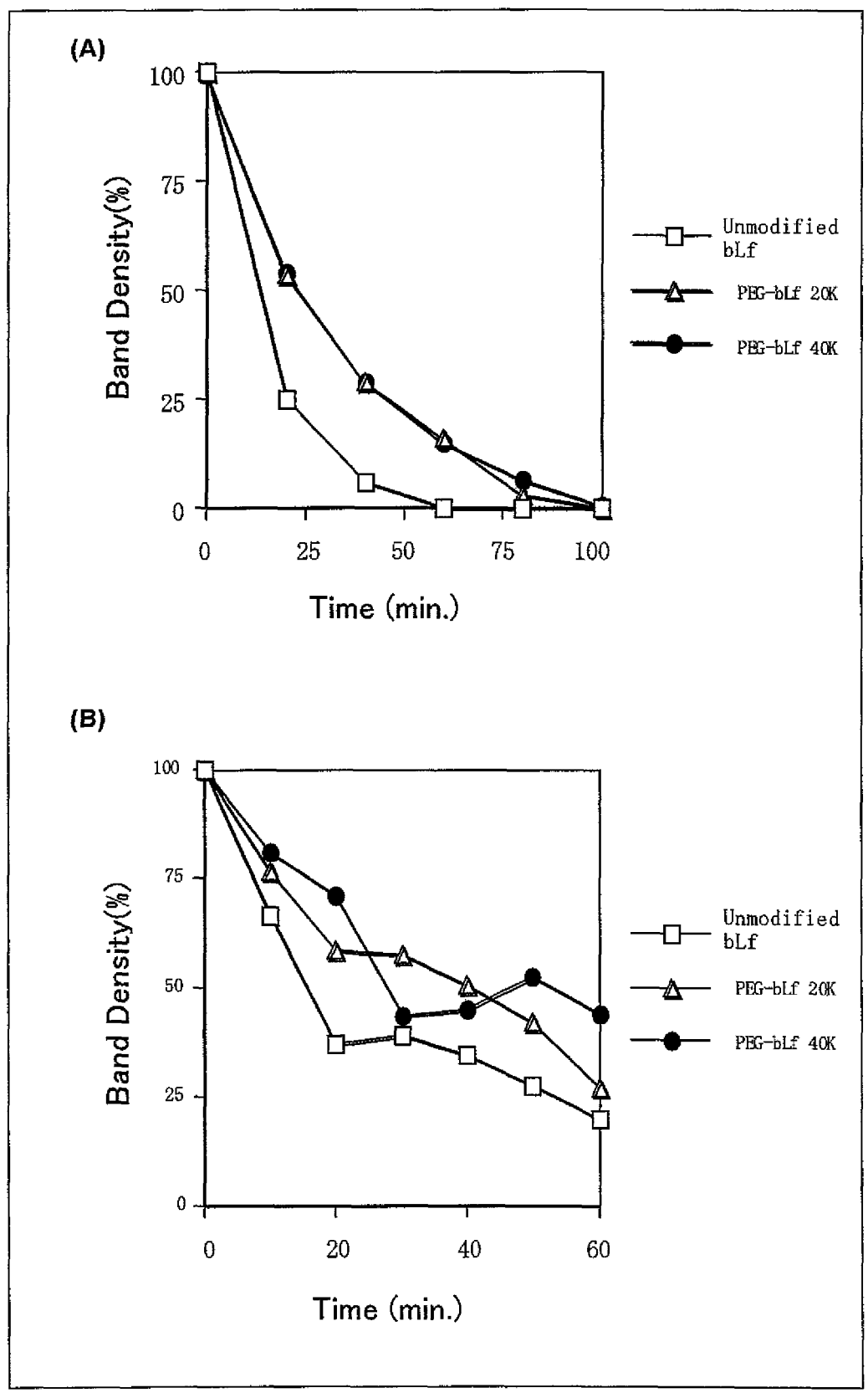
FIG. 12 is a graphic representation wherein the decomposition with time of pegylated bLf with pepsin or trypsin is compared with the decomposition of unmodified bLf.

FIG. 12 shows the results of analysis wherein the electrophoresed image in FIG. 8 was incorporated with a scanner and then the density of the bands was analyzed with the NIH image in order to semi-quantitatively show the decomposition with time of intact pegylated bovine lactoferrin (shown by a mark * in FIG. 8). The density of the band at each time point is shown on the ordinate as relative values to the density at time 0 (minute) as 100%. The time for treatment with each enzyme is shown on the abscissa. The decomposition of the pegylated bovine lactoferrin with pepsin (panel A) and trypsin (panel B), to both of 20k-PEG-bLf and 40k-PEG-bLf, tended to be gentle as compared with decomposition of unmodified bLf. Specifically, the degrees of remaining pegylated bLf after digestion with, e.g., pepsin were about 2-fold and about 5-fold relative to those of the unmodified bLf after digestion for 20 minutes and 40 minutes, respectively.

From the results described above, it can be seen that pegylated bLf, as compared with unmodified bLf, is significantly made less susceptible to the action of pepsin and trypsin.

8. Measurement of Iron-Binding Ability of Pegylated Lactoferrin

Lactoferrin is a nonheme, iron-binding glycoprotein having a molecular weight of 80,000 and consisting of two domains called N-lobe and C-lobe. In the presence of carbonate ion ($CO_3^{2-}$), it has an ability to reversibly chelate-bond two iron ions ($Fe^{3+}$) per protein molecule (Anderson, et al., Nature, 344, 784-78 (1990)). The iron binding ability of lactoferrin was measured in the following manner.

Apo-form lactoferrin was prepared by releasing iron ions ($Fe^{3+}$) from holo-form lactoferrin. Then, iron ions ($Fe^{3+}$) were added to the lactoferrin in the presence of carbonate ion ($CO_3^{2-}$) to prepare iron-rebound lactoferrin. The iron contents and protein concentrations of the apo-form lactoferrin and iron-rebound lactoferrin were measured to determine the amounts of iron bound thereto. The measurement was carried out specifically as follows: The apo-form lactoferrin was prepared by dialyzing bLf (unmodified bovine lactoferrin), 20k-PEG-bLf and 40k-PEG-bLf obtained in the experiment as described in Section 5 above against 0.1 M citric acid buffer, pH 2.1, for 24 hours and then dialyzing them against distilled water for further 24 hours. The iron-rebound lactoferrin was prepared by dialyzing the apo-form lactoferrin against a phosphate buffer, pH 7.5, containing 0.001% ammonium iron citrate, 50 mM sodium carbonate and 50 mM sodium chloride for 24 hours, and then dialyzing it against distilled water and then against a phosphate buffer, pH 7.5, containing 50 mM sodium chloride for 24 hours, in order to remove excessive iron ions. A negative control, BSA (bovine serum albumin), was subjected to the same operation. For measuring protein-bound iron ions by a calorimetric method, a serum iron measurement kit "Fe C-Test Wako" (Wako Pure Chemical Industries, Ltd.) was used. The ability to bind iron was calculated as the amount of iron bound per 1 mg of protein quantified by the Bradford method. The results are shown in Table 2.

TABLE 2

Amount of iron bound to PEGylated lactoferrin

| Protein | Amount of bound iron (ng) | | Relative binding capacity (%) |
| --- | --- | --- | --- |
| | apo-form | iron-rebound form | |
| bLf | ND | 909.0 | 100 |
| PEG-bLf 20k | ND | 1128.8 | 124 |
| PEG-bLf 40k | ND | 1092.1 | 120 |
| BSA | ND | ND | — |

ND: not deteced.

With respect to the apo-form, the amount of bound iron in every protein was below the detection limit. With respect to the iron-rebound form, on the other hand, iron binding was detected except for the negative control, BSA. With respect to 20k-PEG-bLf and 40k-PEG-bLf, the comparable amounts of bound iron as in the unmodified bLf were detected, and it was revealed that the activity to bind iron ions was not lost by pegylation.

This application is based on Japanese Patent Application No. 2005-258103 filed Sep. 6, 2005, and the entire disclosure and claims of Japanese Patent Application No. 2005-258103 are included in this specification.

The invention claimed is:

1. A biologically active complex of lactoferrin with a branched non-peptide hydrophilic polymer, the complex being represented by the following formula [II]:

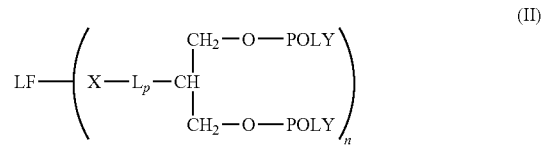

wherein LF is lactoferrin, X is a linkage generated by reaction of functional groups, L is a linker, POLY is a non-peptide hydrophilic polymer, p is 0 or 1, and n is an integer of 1 to 10; or by the following structure:

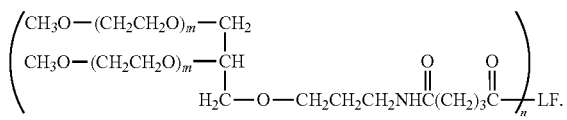

wherein m is an integer such that each of the branched non-peptide hydrophilic polymer has a molecular weight of about 20 kDa or 40 kDa, and n is an integer of 1 to 10.

2. The complex according to claim 1, wherein the complex is represented by the following formula [II]:

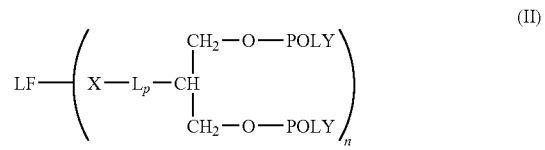

wherein LF is lactoferrin, X is a linkage generated by reaction of functional groups, L is a linker, POLY is a non-peptide hydrophilic polymer, p is 0 or 1, and n is an integer of 1 to 10.

3. The complex according to claim 2, wherein the complex has the following structure:

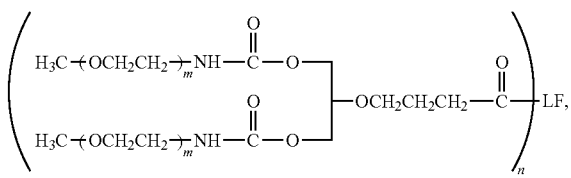

wherein m is an integer such that each of the branched non-peptide hydrophilic polymer has a molecular weight of about 10 kDa or 40 kDa, and n is an integer of 1 to 10.

4. The complex according to claim 1, wherein POLY is selected from the group consisting of poly(alkylene glycol), poly(oxyethylated polyol), poly(olefinic alcohol), poly(vinyl pyrrolidone), poly(hydroxyalkyl methacrylamide), poly(hydroxyalkyl methacrylate), poly(saccharide), poly(α-hydroxy acid), poly(vinyl alcohol), polyphosphazene, polyoxazoline, poly(N-acryloyl morpholine), and modified products thereof, copolymers thereof and mixtures thereof.

5. The complex according to claim 1, wherein POLY is polyethylene glycol or a modified product thereof.

6. The complex according to claim 1, which maintains iron chelate ability of at least 30% of natural lactoferrin.

7. The complex according to claim 1, wherein n is an integer of 1 to 5.

8. The complex according to claim 1, wherein the complex has the following structure:

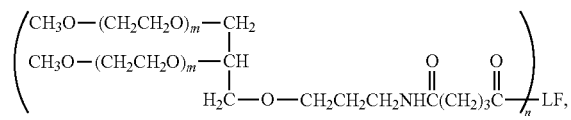

wherein m is an integer such that each of the branched non-peptide hydrophilic polymer has a molecular weight of about 20 kDa or 40 kDa, and n is an integer of 1 to 10.

9. A pharmaceutical composition comprising the biologically active complex of lactoferrin with a branched non-peptide hydrophilic polymer according to claim 1 and a therapeutically inert base and/or an additive.

10. A method of purifying a biologically active complex of lactoferrin with a branched non-peptide hydrophilic polymer, the method comprising subjecting a biologically active complex of lactoferrin with a branched non-peptide hydrophilic polymer contained in a sample to:

i) a step of adsorbing the complex onto a cation exchange carrier to concentrate it and then applying the resulting concentrate to a gel filtration carrier, or ii) a step of applying the complex onto a cation exchange gel filtration carrier.

11. A method of producing a biologically active complex of lactoferrin with a branched non-peptide hydrophilic polymer according to claim 2, the method comprising the step of reacting lactoferrin with a branched non-peptide hydrophilic polymer represented by the following formula [IV]:

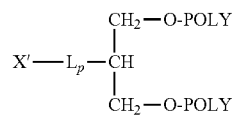

wherein X' is a functional group, L is a linker, POLY is a non-peptide hydrophilic polymer, and p is 0 or 1, under such conditions as to generate a covalent bond therebetween.

12. The production method according to claim 11, wherein lactoferrin and the branched non-peptide hydrophilic polymer are added in a molar ratio of 1:1 to 1:100 to the reaction solution.

13. The production method according to claim 11, wherein the reaction step is carried out under the conditions of pH 4 or more, a temperature of 0 to 40° C. and a time of 1 minute to 24 hours.

14. The production method according to claim 11, wherein the branched non-peptide hydrophilic polymer represented by formula [IV] has a molecular weight of about 10 kDa or 40 kDa and a structure of:

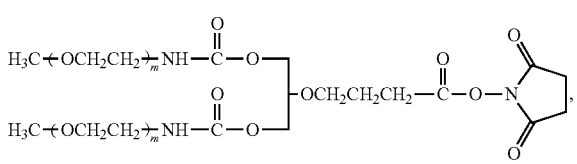

wherein m is an integer.

15. A method for treating or preventing a disease or symptom associated with lactoferrin deficiency, comprising: administering to a subject in need thereof a pharmaceutical preparation comprising the biologically active complex of lactoferrin with a branched non-peptide hydrophilic polymer according to claim 1.

16. A method of producing a biologically active complex of lactoferrin with a branched non-peptide hydrophilic polymer according to claim 8, the method comprising the step of reacting lactoferrin with a branched non-peptide hydrophilic polymer represented by the following formula:

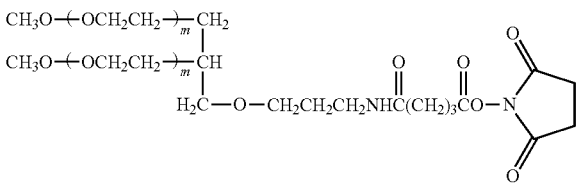

wherein m is an integer such that each of the branched non-peptide hydrophilic polymer has a molecular weight of about 20 kDa or 40 kDa, under such conditions as to generate a covalent bond therebetween.

17. The production method according to claim 16, wherein lactoferrin and the branched non-peptide hydrophilic polymer are added in a molar ratio of 1:1 to 1:100 to the reaction solution.

18. The production method according to claim 16, wherein the reaction step is carried out under the conditions of pH 4 or more, a temperature of 0 to 40° C. and a time of 1 minute to 24 hours.

* * * * *